United States Patent
Kontiola

[11] Patent Number: 6,093,147
[45] Date of Patent: Jul. 25, 2000

[54] APPARATUS FOR MEASURING INTRAOCULAR PRESSURE

[76] Inventor: Antti Kontiola, Teuvo Pakkalan tie 8L I11, Helsinki FIN-00400, Finland

[21] Appl. No.: 09/255,465

[22] Filed: Feb. 22, 1999

[51] Int. Cl.$^7$ .................................................. A61B 3/16
[52] U.S. Cl. ................................................................ 600/405
[58] Field of Search .................................. 600/399, 405, 600/406

[56] References Cited

U.S. PATENT DOCUMENTS 5,165,409 11/1992 Coan .
5,174,292 12/1992 Kursar .
5,176,139 1/1993 Fedorov et al. .
5,190,042 3/1993 Hock .

FOREIGN PATENT DOCUMENTS 0 584 929 A1 3/1994 European Pat. Off. .

*Primary Examiner*—Max Hindenburg
*Attorney, Agent, or Firm*—Skinner and Associates

[57] ABSTRACT

An apparatus for measuring intraocular pressure. The apparatus comprises a probe (11), which is propelled at a constant velocity to impact the eye, and includes a device (12, 7) for continuously determining the velocity of the probe. The velocity is used to derive the intraocular pressure.

15 Claims, 4 Drawing Sheets

5 mmHg 60 mmHg

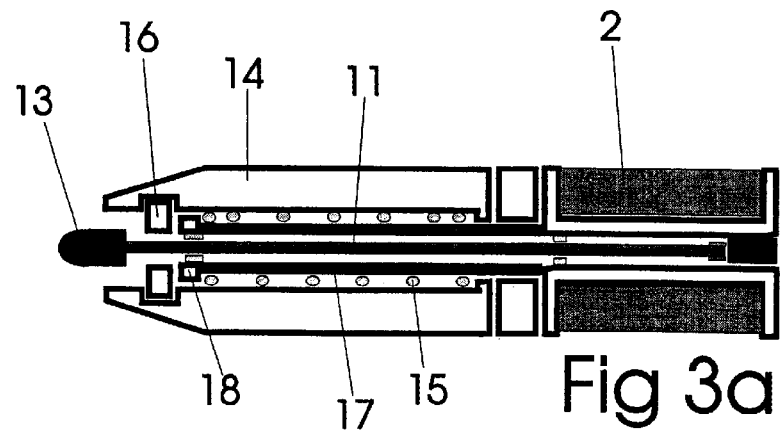
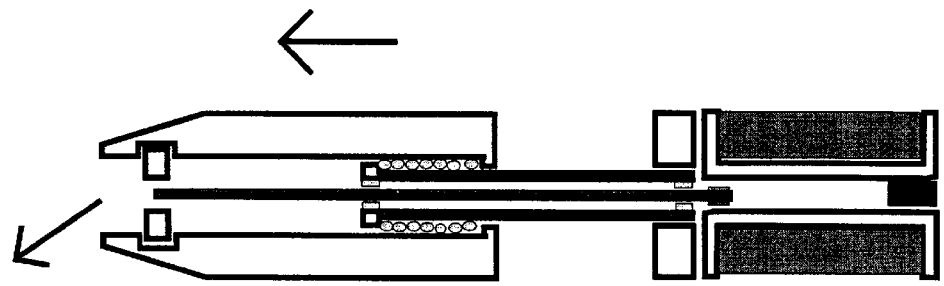
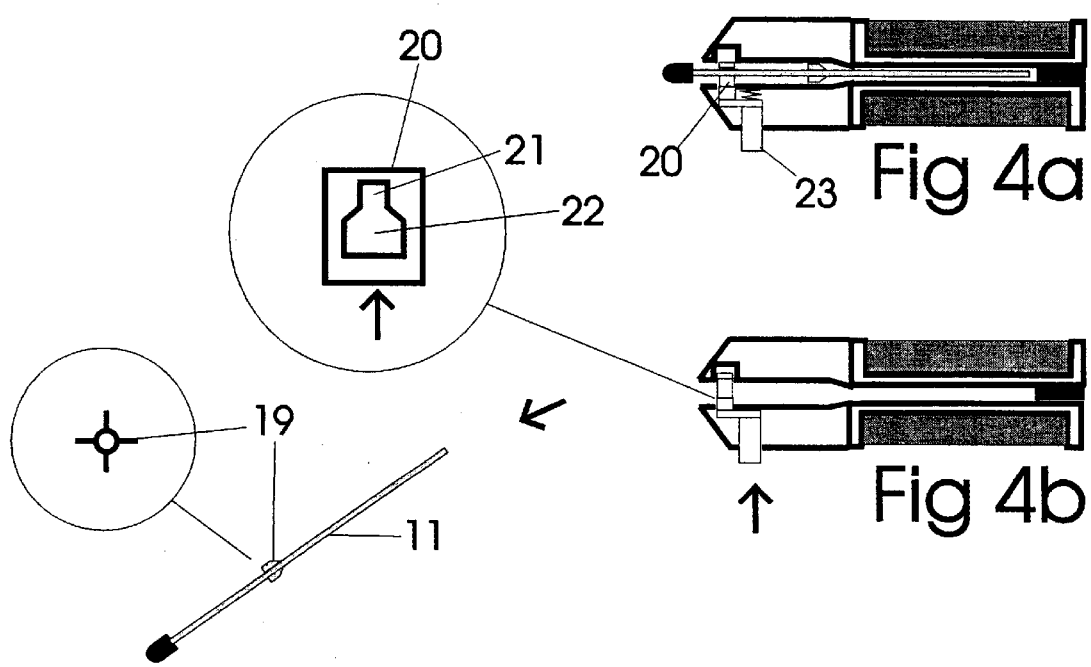

APPARATUS FOR MEASURING INTRAOCULAR PRESSURE

FIELD OF THE INVENTION

The present invention relates to an apparatus for measuring intraocular pressure. The apparatus is based on an understanding of the laws governing the impact of an object with the eye.

BACKGROUND OF THE INVENTION

Intraocular pressure is generally measured using a tonometer, which is placed on the surface of the cornea and measures the elasticity of the latter using various methods (Goldmann's tonometer, Schiötz's tonometer, etc.). Two of the most commonly used principles are measurement of the force required to applanate a certain area of the surface or measurement of the diameter of the area applanated by a known force. These methods require the patient's cooperation and cannot be applied without general anaesthesia to small children, persons suffering from dementia, or animals.

Methods such as U.S. Pat. Nos. 5,148,807, 5,279,300 and 5,299,573, have also been developed, in which the surface of the cornea is not touched, the intraocular pressure being measured instead by means of a water or air jet or various waves. Such methods are technically complex and thus expensive. Meters operating on the air jet principle are widely used by opticians, but their expense has prevented their extensive use by general practitioners.

U.S. Pat. No. 5,176,139 also describes a method in which a freely-falling ball is dropped onto the eyelid and the height of the ball's rebound is measured.

SUMMARY OF THE INVENTION

The present invention is intended to create a simple, cheap and precise apparatus, which permits intraocular pressure to be measured even in uncooperative patients, who can be restrained only momentarily. In addition, the meter is suitable for extensive screening campaigns, as measurement is rapid and demands neither a local anaesthetic nor specially trained personnel. It is also aimed at providing home monitoring for patients with intraocular pressure complaints.

These and other benefits and advantages of the present invention are achieved by means of a method and equipment according to the invention, the characteristics of which are detailed in the accompanying claims.

The invention is next described. The probe is set in motion, which is either predetermined or otherwise defined with sufficient accuracy. When the probe impacts the eye or the closed eyelid, the motion of the probe changes. According to the invention, a suitable means, for example, an apparatus according to the invention, is used to measure the continuous motion of the probe, from which the intraocular pressure is then derived. Thus, an overall analysis is made of the motion during and after impact, including the effects of gravitation and friction on the probe. In this way, the analysis monitors the motion comprehensively and derives the intraocular pressure by applying known physical laws.

The probe with its sensor is light and the velocities used are low, so that there is no risk of eye damage. The method can also be applied when the eyelid is closed. Thanks to the probe's low velocity and mass, anaesthetization of the eye is not required under any measurement circumstances. The meter can be calibrated to different standards, by comparing the results with those obtained by other methods or by using experiential methods.

An apparatus according to the invention contains few components. The apparatus can be designed as a small entity that can easily be held in the hand. Its operation is simple and does not involve high costs. The invention is more accurate than previous apparatuses and makes it possible to allow for random changes and also for quantities, e.g., friction that changes as the apparatus ages, that vary over longer periods of time.

BRIEF DESCRIPTION OF THE DRAWINGS

Next, the invention is described in detail with reference to the drawings, in which

FIG. 3a shows a detail of an apparatus according to the invention and a closer view of the operation of the probe in the initial situation;

FIG. 3b shows the solution in FIG. 3a in a case in which an interchangeable component is used on the front of the probe;

FIGS. 4a and 4b show solutions according to FIGS. 3a and 3b, when the entire probe is disposable.

DETAILED DESCRIPTION OF THE INVENTION

Figure 1:
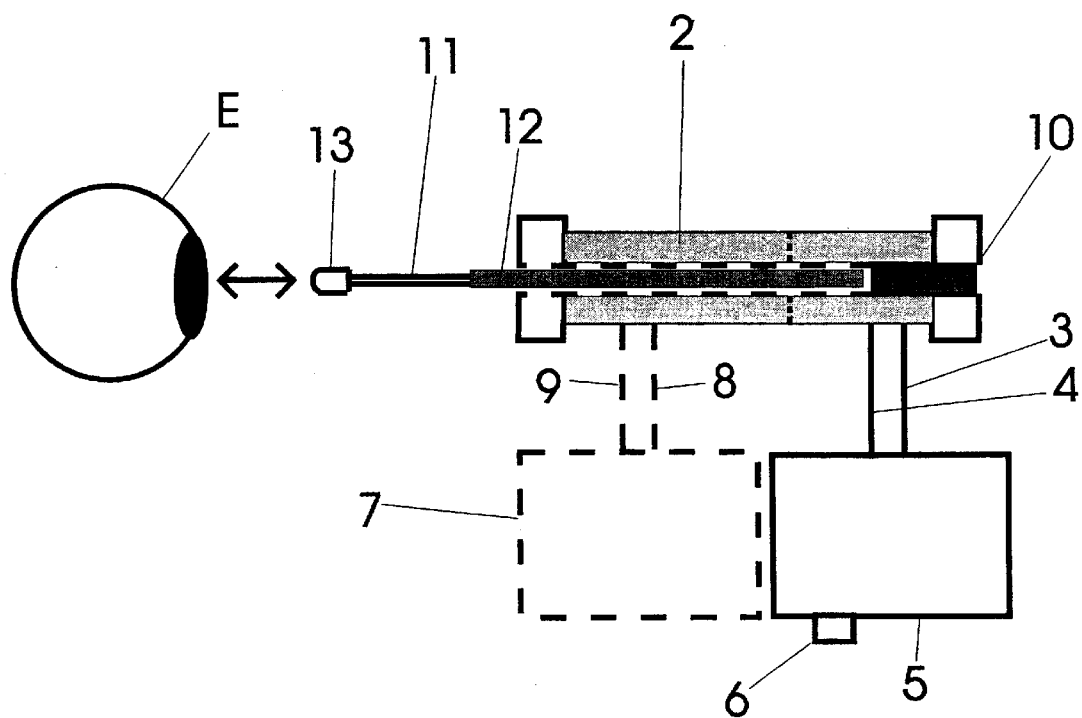
FIG. 1 shows a diagrammatic, and in many respects simplified side view of an apparatus according to the invention.

FIG. 1a shows a greatly simplified view of an apparatus according to the invention, intended to measure intraocular pressure in accordance with the invention. For example, the case in which the components are placed, has been entirely excluded from the drawing. The figure has also been simplified in other ways.

Thus, meter 1 comprises only a few basic components and is therefore extremely simple. An apparatus according to the invention includes a coil 2, of the solenoid type. Current leads 3, 4, a current supply 5 and a switch 6 to start the operation of the meter are connected to coil 2 in a manner that is, as such, known. The apparatus also has leads 8, 9 connected to the same coil 2, the leads being shown here by broken lines and the leads being connected to a measurement component 7 equipped with a display device. If desired, the coil 2 can be divided into two separate parts. This is illustrated by the broken running through the coil. A later description will show that both alternatives are practicable.

Figure 5:
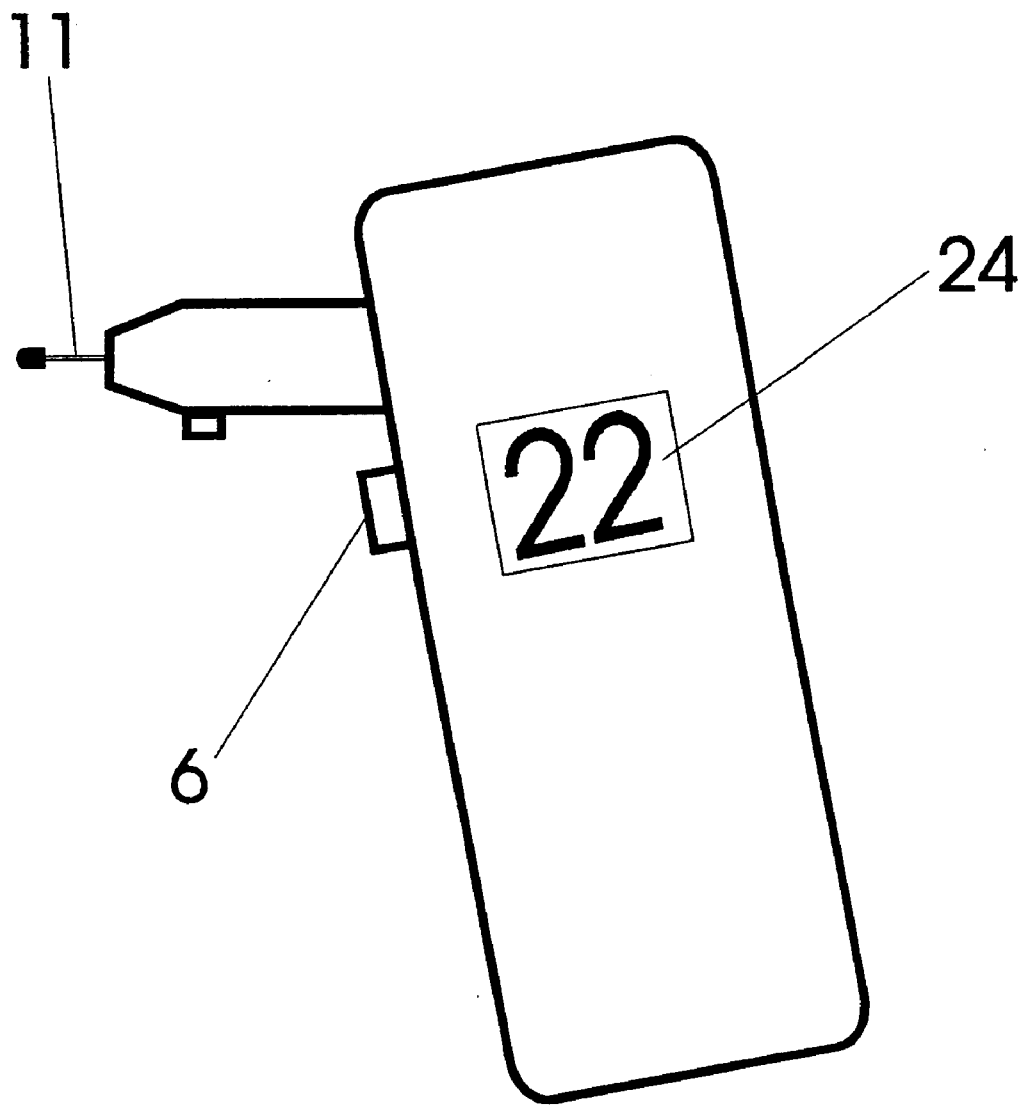
FIG. 5 shows a practical embodiment of an apparatus according to the invention.

It is clear that, in practice, an apparatus according to the invention can be assembled, for example, according to FIG. 5, to form a very small and easily used device. The electrical and other connections and arranged inside the case in a manner proposed by those versed in the art, so that the measurement can be carried out quickly and precisely and that the display shows the result obtained immediately after the physical performance of the measurement.

The apparatus includes, inside coil 2 or at the end of it, a non-permanently magnetized counter piece 10. A rod-like probe 11 is mounted in bearings in the case of the apparatus, which is not shown in FIG. 1, and has at its end a permanent magnet or permanently magnetized component 12, located physically at the inner end of, or even inside, probe shaft 11.

At the very start of the measurement, permanent magnet 12 acts to create a weak force to secure the probe inside the coil 2, due to the attraction between components 10 and 12. It is evident that parts 11 and 12 may be combined into only one and uniform part.

The electrical connections and directions of the current in magnet 12 and coil 2 are arranged so that closing switch 6 simultaneously makes a current circuit to coil 2, creating a repelling force in magnet 12 and causing magnet 12 and shaft 11 to move away from coil 2. It is clear that the pulse of current induced in coil 2 is essentially extremely short and independent of the duration of the closure of switch 6 that completes the electrical circuit, so that it will ensure a standard impulse to probe 11.

The moving component, i.e. the probe, can be of any suitable type and can be equipped, for example, with a suitable blunt, clean and interchangeable point 13. Point 13 is always replaced for a new measurement, to meet the requirements of hygiene. However, as will be describe later, shaft 11 can act in its entirety as the probe, including the point component and thus shaft 11 can be replaced with a new one, before beginning a new measurement. In other words, the moving component can be entirely disposable along with its magnetized part or magnet.

Once the coil has been given a short current pulse to set shaft 11 into essentially standard motion towards the eye E, the magnet part 12 connected to shaft 11, or especially in the case of a disposable probe, the shaft 11 that is possibly itself magnetized, moves inside coil 2 and induces a voltage in the coil, which is led by leads 8 and 9 to be processed by the electronics of apparatus according to the invention, after which the numerical value of the intraocular pressure derived from it is able to be read from a numerical display on a suitable display device. FIG. 5 illustrates the appearance of an apparatus according to the invention and also shows a display device, the display of which shows the value 22 of the intraocular pressure.

Figure 2A:
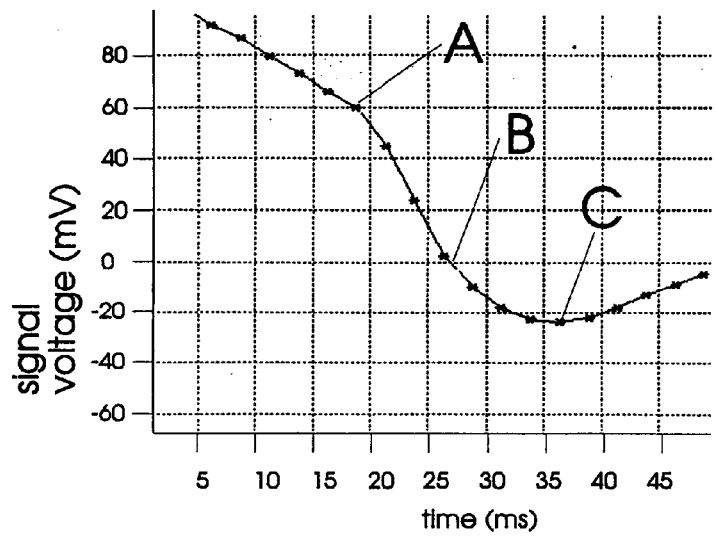
FIGS. 2a and 2b show the velocity curves obtained in practical tests with an apparatus operating on the principle shown in FIG. 1, at intraocular pressures of and correspondingly 60 mm Hg.
Figure 2B:
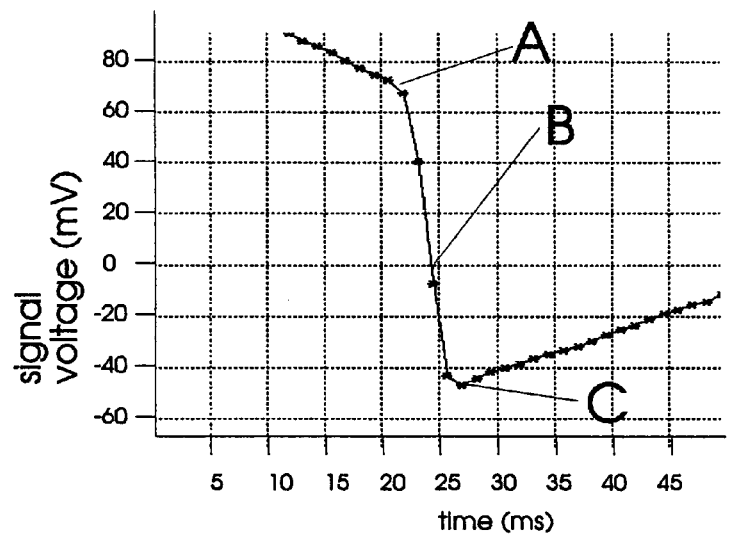

FIGS. 2a and 2b show two examples of velocity curves obtained, under test conditions, with a pig's eye pressurized to 5 and correspondingly 60 mm Hg. As the figures clearly show, the velocity clearly varies in the case of eyes with different pressures. The velocity (or strength of signal) is shown on the vertical axis, while the horizontal axis shows the time in milliseconds. At point A the probe strikes the surface of the eye. The probe pushes the surface of the eye slightly inwards and at point B the probe rebounds, separating from the surface of the eye at point C.

FIGS. 3a and 3b show how an interchangeable point 13 of a probe can be detached from shaft 11 using a simple grip, without touching it by hand and correspondingly FIGS. 4a and 4b show how an entirely interchangeable probe is replaced with a new one.

The shaft of the probe is surrounded by a tube-like part 17, which is suitably permanently attached to the case of the apparatus, e.g., by a lock ring (not shown). The shaft 11 of the probe moves inside this sleeve linearly and precisely. An elongated sleeve-like component 14 is located on top of tube-like part 17, with a spring 15 between the flange-like front section 18 of part 17 and the rear section of sleeve 14. The front section of sleeve 14 is closed by ejector component 16, which may be, for example, a plate or similar with a hole, through which shaft 11 can travel.

FIG. 3a shows the initial situation when changing of the point part 13 at very start of, or after a measurement. By gripping 14 and pulling it out from the apparatus against the force of spring 15 causes the point 13 to push strongly against ring 16, and, in a situation in which shaft 11 can no longer slide outwards, the point part detaches and flies off. This situation is illustrated in FIG. 3b.

FIG. 4a shows a situation corresponding to that in FIG. 3a, when a disposable probe 11 is used, which is replaced after a measurement. The shaft 11 of the probe has a widened part, which may be of any kind at all, but can be, for example, as shown in the shape of a 'wing' 19 that extends outwards from the shaft in several places. Retention plate 20 has a narrower part 21 and a wider part 22. Button 23 is linked to plate 20 and, when pressed, causes the wider part 22 to move next to the shaft 11, in place of the narrower part 21 that is normally there, when the probe in its entirety is able to leave the apparatus. A new probe is set in place in the same position, after which the released button 23 ensures that the narrower part 21 moves to close the exit of the probe from the device. It is self-evident that that a great many alternative ways of retaining and releasing the relevant component can be found in other areas of technology and that the above description is in no way restrictive.

When measuring intraocular pressure, the apparatus is supported so that shaft 11 and point part 13 at the end of it are aimed at the eye to be measured, at a distance of a few millimeters from the eye. Pressing on trigger 6 creates, for example, a pulse controlled by a processor, which causes shaft 11 with point 13 to move towards the eye and strike it, and to rebound from it, in a manner depending on the intraocular pressure. Electronics continuously measure the velocity and convert the values obtained into a form visible on the display, as described above.

In the case of an interchangeable point, once the measurement has been made the sleeve or case component 14 is gripped and pulled away from the apparatus, against the force of spring 15, when point part 13 detaches and flies off, as shown in FIG. 3b. Spring 15 returns sleeve 14 to its original position. After this, a new, clean, point component is placed on the end of shaft 11 for the next measurement. Shaft 11 returns to its original position, for instance, by simply turning the meter to a position, in which component 14 is upwards. Gravity then returns shaft 11 and its magnet to a position with magnet 12 attached to counter piece 10, where the attraction of magnet 12 retains it. On the other hand, it is also possible to use a pulse in the opposite direction sent to the coil, which creates a force that pulls the shaft back to the initial situation. This ensures that the initial situation is always the same and comparable.

In cases in which a disposable probe is used, a possibility to give a current pulse to the coil can be arranged in connection with locking button 23. For example, pressing button 23 opens the path for the disposable moving component 11 to leave the apparatus while the same current impulse to the coil induces an ejecting force in component 11. Thus, no other measures are required for component 11 to fly out of the apparatus.

The device can be used, by means of a possible additional component, by supporting the meter at the desired distance from the point of the eye being measured. This will additionally ensure the comparability of different measurements.

The invention permits many possible adaptations not described above.

As stated above, an apparatus according to the invention is extremely cheap, simple and reliable. Expensive moulding technology is not even required to manufacture the apparatus, because, if necessary, the apparatus can be placed inside a simple case manufactured for some other purpose. Operation of all the functions of the apparatus is so easy, and its principle of such simplicity and operational reliability, that practically no training is needed to use it.

The invention is not limited to the form described and in the drawings, but may be adapted within the scope of the accompanying claims.

What is claimed is:

1. An apparatus for measuring intraocular pressure, comprising
   (a) a probe,
   (b) a propulsion device adapted for propelling the probe at an essentially constant departure velocity and force, and
   (c) data processing and display devices adapted for recording the motion of the probe.

2. The apparatus of claim 1, wherein the propulsion device comprises a coil and a shaft, the shaft having an attached magnet, whereby a current flowing through the coil causes a repelling force in the magnet.

3. The apparatus of claim 1, wherein the data processing and display devices include a coil and a measuring part, wherein a magnet connected to the probe moves inside of the coil, and wherein the measuring part records the variations in voltage and current induced in the coil by the magnet.

4. The apparatus of claim 2, further comprising a current supply device adapted for sending a current pulse of essentially constant size and duration through the coil.

5. The apparatus of claim 2, wherein the coil is connected to a counter piece, and wherein the counter piece and the magnet initially secure the probe inside the coil.

6. The apparatus of claim 2, wherein the probe is supported and located within a suitable case, wherein the shaft and the magnet are supported and mounted in bearings in a separate, detachable sleeve-like component.

7. The apparatus of claim 6, further comprising a movable component and a spring, wherein the movable component acts linearly in relation to the sleeve-like component and against a spring force, the movable component being equipped at its outer end with a device for detaching an interchangeable point from an end of the shaft by means of moving the movable component.

8. The apparatus of claim 1, further comprising a single coil, wherein a current pulse fed to the coil provides the probe with kinetic energy, and wherein the motion of the magnet is recorded using the same coil.

9. The apparatus of claim 1, further comprising two separate coils, wherein one of the two coils propels the probe and the other of the two coils records the velocity of the probe.

10. The apparatus of claim 1, wherein the probe is disposable and is changed in its entirety between measurements.

11. The apparatus of claim 10, further comprising a locking button and a coil, wherein pressing the locking button releases the disposable probe and simultaneously sends a current impulse to the coil to eject the probe.

12. The apparatus of claim 2, wherein the shaft is set and retained in place either by means of gravity or by sending a current impulse to the coil in the opposite direction to the current flow that causes a repelling force in the magnet.

13. The apparatus of claim 2, in which the shaft and the magnet form one part.

14. An apparatus, comprising:
    (a) a probe having a magnet;
    (b) a propulsion device for inducing a predetermined velocity to the probe, the propulsion device including a coil surrounding the magnet; and
    (c) a recording device for recording the motion of the probe, the recording device including a coil for sensing the motion of the magnet.

15. An apparatus for measuring intraocular pressure, comprising:
    (a) a probe including a shaft having a proximal end and a distal end, a magnet attached to the proximal end of the shaft, and a point part at the distal end of the shaft for contacting an eye;
    (b) a counter piece for holding the magnet in a predetermined initial position;
    (c) a propulsion device for inducing a predetermined velocity to the probe, the propulsion device including a coil surrounding the magnet of the shaft, wherein a current pulse in the coil moves the probe from the initial position to an extended position;
    (d) a recording device for recording the motion of the probe, the recording device including a coil, wherein the motion of the magnet generates a measurable current in the coil; and
    (e) a case containing the probe, the case including:
        (i) a separate, detachable sleeve having bearings, the shaft of the probe being supported by the bearings;
        (ii) a spring; and
        (iii) a movable sleeve having a device for detaching the point part from the distal end of the shaft by moving the movable component against the spring.

* * * * *